(12) United States Patent
Odiwo

(10) Patent No.: US 6,918,770 B2
(45) Date of Patent: Jul. 19, 2005

(54) INFANT NURTURING MEDICAL DEVICE

(75) Inventor: Edith Lamira Odiwo, Wappingers Falls, NY (US)

(73) Assignee: BrightWave Enterprises, LLC, Wappingers Falls, NY (US)

(*) Notice: Subject to any disclaimer, the term of this patent is extended or adjusted under 35 U.S.C. 154(b) by 0 days.

(21) Appl. No.: 10/642,269

(22) Filed: Aug. 18, 2003

(65) Prior Publication Data

US 2004/0077287 A1 Apr. 22, 2004

Related U.S. Application Data

(60) Provisional application No. 60/404,157, filed on Aug. 19, 2002.

(51) Int. Cl.[7] .............................................. G09B 23/28
(52) U.S. Cl. ........................ 434/262; 434/266; 434/267; 600/22
(58) Field of Search ................................. 434/267, 262; 600/22; 5/93.1, 93.2, 94–97, 98.1, 98.2, 98.3, 99.1

(56) References Cited

U.S. PATENT DOCUMENTS

| | | | | |
|---|---|---|---|---|
| 2,551,433 | A | * | 5/1951 | Graves ........................ 434/273 |
| 3,335,433 | A | * | 8/1967 | Stopek .......................... 5/105 |
| 3,563,229 | A | | 2/1971 | Petrusson |
| 3,888,233 | A | | 6/1975 | Ware |
| 4,166,337 | A | | 9/1979 | Kosicki |
| 4,206,567 | A | * | 6/1980 | Cieslak ........................ 446/73 |
| 4,411,629 | A | * | 10/1983 | Voights ....................... 434/266 |
| 4,736,847 | A | * | 4/1988 | Wang .......................... 206/457 |
| 4,750,474 | A | | 6/1988 | Dukhan |
| 4,874,344 | A | * | 10/1989 | Kanter ......................... 446/268 |
| 4,883,442 | A | * | 11/1989 | Kaplan ........................ 446/320 |
| 5,038,426 | A | * | 8/1991 | Boretski ........................ 5/93.1 |
| 5,073,140 | A | | 12/1991 | Lebensfeld |
| 5,104,328 | A | * | 4/1992 | Lounsbury .................. 434/273 |
| 5,224,923 | A | | 7/1993 | Moffett |
| 5,453,077 | A | | 9/1995 | Donnelly |
| 5,569,131 | A | * | 10/1996 | Giulianelli ..................... 482/77 |
| 5,946,725 | A | * | 9/1999 | Shatzkin et al. ............... 2/106 |
| 6,007,342 | A | | 12/1999 | Tjolsen |
| 6,238,263 | B1 | | 5/2001 | Bennett |
| 6,443,885 | B1 | * | 9/2002 | Schuler ........................ 600/22 |
| D470,546 | S | * | 2/2003 | Torrejon-Romani ........ D21/595 |
| 6,544,097 | B1 | | 4/2003 | Bain |
| 6,758,676 | B2 | * | 7/2004 | Eggert et al. ................ 434/262 |

FOREIGN PATENT DOCUMENTS

GB          2060412 A  *  5/1981  ............ A63H/3/00

* cited by examiner

Primary Examiner—Jessica Harrison
Assistant Examiner—Dmitry Suhol
(74) Attorney, Agent, or Firm—Johnson & Associates, PC; Chauncey B. Johnson, Esq.

(57) ABSTRACT

An Infant Nurturing Device for performing parent-infant attachment comprising a pouch area (25), a proportional external pouch covering (21), means for producing simulated parental body temperature (770), means for producing simulated parental heartbeat (750), means for producing simulated parental voice (780), means for producing simulated parental breathing (760) and a controller (740). The Infant Nurturing Device of the present invention is capable of performing adequate "Kangaroo Care" parent-infant attachment in the absence of biological parents.

19 Claims, 4 Drawing Sheets

INFANT NURTURING MEDICAL DEVICE

RELATED PATENT APPLICATION

This application benefits from the earlier filing date of a U.S. provisional application, Ser. No. 60/404,157, filed on Aug. 19, 2002.

BACKGROUND OF THE INVENTION

1. Field of the Invention

The present invention relates generally to an Infant Nurturing Device used for performing parent-infant "Kangaroo Care" attachment in the absence of biological parents. Specifically, the present invention relates to an Infant Nurturing Device capable of performing parent-infant attachment by transferring simulated parental body temperature, simulated parental heartbeat, simulated parental voice and simulated parental breathing in the absence of biological parents.

2. Description of Related Prior Art

The birth of a newborn child, a full-term infant or a pre-term infant can be an exciting time in the lives of parents and relatives. Enhanced parent-infant attachment or bonding is crucial for continuous and successful development of a newborn infant, especially in the case of a pre-term infant. Child development research has directed some attention towards the importance of parent-infant attachment during the early stages of infancy. Research has shown that newborns, including pre-term infants, have a uniquely innate form of interaction and attachment with their parents early on in their developmental process. That is, attachment between a newborn infant and the infant's parent, especially the infant's mother, provides essential emotional and psychological needs required for orderly infant development and maturity.

In the past, the importance of an infant's emotional and psychological needs through parent-infant attachment was not fully understood in the medical profession and thus not well documented. Such level of ignorance has since changed, as contemporary child development research has gradually established the importance of a parent's, such as a mother's, voice, heartbeat, breathing and body temperature to the early development of a new-born infant. Contemporary research has also established that an infant recognizes his or her birth mother through the mother's scent, voice and heartbeat, etc., and is thus capable of noticing the presence or absence of the mother.

The absence of an infant's mother affects the infant's security, drastically shakes the infant's confidence, and often has an adverse effect on the orderly development of the infant. In contrast, when an infant's mother is present, the infant benefits from the warmth of the mother's body temperature, the soothing tone of the mother's voice and the rhythm of both the mother's heartbeat and breathing. Thus, it is well established that parent-infant attachment is necessary for fulfilling the emotional and psychological needs, and for the orderly development of a newborn infant. The attachment phenomenon, which promotes emotional, psychological and orderly development of an infant is even more important and pronounce when dealing with premature infants. As is well known, the birth of a premature infant places enormous stress and difficulties on parents and supportive relatives. It is not uncommon for a mother to feel extremely helpless and often depress when repeatedly confronted with challenges and complexity associated with premature infants. Although advances in technology have played a significant part in the survival rate of premature infants, research has shown that skin-to-skin attachment between a parent, for example, a mother, and a premature infant contributes significantly to the survival rate of the infant. Thus, along with technology advances, the medical profession has incorporated the parent-infant attachment procedure in its overall developmental therapy for full and pre-term newborn infants.

The technique used by parents, especially mothers, in performing the parent-infant attachment procedure is widely known in medical circles as "Kangaroo Care". Performance of the "Kangaroo Care" approach, which is often required of mothers for orderly development of infants, is applicable to both full and pre-term infants. The "Kangaroo Care" approach is so-named because the infant is positioned upright and close to a parent's chest to simulate a baby Kangaroo in its mother's pouch. "Kangaroo Care" is reported to have first begun in Columbia, South America and was initiated by Doctors Martinez and Rey, whose decisions to use this approach was based on the absence of adequate medical equipment and the increased risks of infection from unsanitized hospital conditions. Hence, mothers were encouraged to transport their pre-term infants from hospitals between their breasts, while feeding the infants with breast milk.

Susan Lugdinton, author of "Kangaroo Care: The Best You Can Do For Pre-term Baby", has proven through extensive research that the "Kangaroo Care" approach has been extremely successful when applied to premature infants. Her research with pre-term infants revealed that intimate cuddling stabilizes heart rate and breathing, conserves an infant's energy and increases milk production in new mothers. Lugdinton research also revealed that the "Kangaroo Care" approach drastically reduces or even prevents Sudden Infant Death Syndrome (SIDS), frequently associated with infants, especially newborn pre-term babies, whom often experience difficulties with coordinating their heart rates with their breathing. Lugdinton also credits "Kangaroo Care" for drastically reducing episodes of apnea in premature infants. In a specific study conducted by Lugdinton at the Massachusetts General Hospital, of the nineteen thousand infants observed, nine infants who showed sign of "less coordinated coupling" died of SIDS. Lugdinton also established a nexus between "Kangaroo Care" attachment and brain development in infants. As an example, after only ten minutes of close contact with parents thirty-week old premature infants experienced an increase in brain cells fusion called neuro synapes. Along with Lugdinton, numerous researches have shown the importance of the "Kangaroo Care" attachment to the overall emotional and psychological development of full-term and pre-term infants.

The current practice of "Kangaroo Care" attachment by the medical profession, which is defined as the practice of pouching an infant, diaper-clad and blanketed, against a parent's bear chest, requires sessions of up to four hours of placing an infant between the breasts of the mother. The attachment sessions create the requisite attachment for enhancing emotional and psychological infant development through exposures to parental heartbeat, parental body temperature, parental breathing rhythm and parental voice recognition. The current "Kangaroo Care" approach requiring the placement of an infant between the breast of a parent to increase emotional and psychological development is extremely limited in at least the following respects: enormous time constraints are placed on parents, especially professional parents, performing "Kangaroo Care" attachment; inadequate parent-to-infant heat transfer and reduced exposure to parental heartbeat rhythm, body temperature and voice due to insufficient time spent between parents and infants; and increase in overall hospital and patient cost. These limitations do not permit full or pre-term infants to receive the adequate emotional and psychological attachment to spur orderly development. For example, reductions in parent-to-infant temperature transfer, parent-to-infant voice transfer and parent-to-infant rhythmic heartbeat transfer has been shown to increase breathing pauses and apnea in infants, decrease infants' oxygen level and often increase the number of slow heart rate spells in infants.

Thus, it would be advantageous to develop a device that is capable of performing parent-infant attachment using the "Kangaroo Care" approach in the absence of biological parents while serving the crucial function of developing full or pre-term infants by creating a sense of security. It would also be advantageous to have a device capable of eliminating time constraints placed on parents performing "Kangaroo Care" attachment, a device capable of transferring simulated parental heart beat rhythm, a device capable of transferring simulated parental body temperature, a device capable of transferring simulated parental voice and a device capable of transferring simulated parental breathing. The Infant Nurturing System Device, "Edith, A Mother in Absentia", of the present invention is capable of providing all the above-listed advantages, which are indeed inextricably linked to the orderly, early-stage development of full and pre-term infants.

SUMMARY OF THE INVENTION

It is therefore, an object of this invention to disclose an Infant Nurturing System Device capable of increasing parent-infant attachment and bonding in the absence of a biological parent, such as a mother.

Another object of this invention is to disclose an Infant Nurturing System Device capable of eliminating time constraints placed on parents performing "Kangaroo Care" Attachment and bonding.

Yet, another object of this invention is to disclose a device capable of transferring simulated parental heartbeat rhythm, a device capable of transferring simulated parental body temperature, a device capable of transferring simulated parental voice and a device capable of transferring simulated parental breathing.

Still, another object of this invention is to disclose an Infant Nurturing System Device capable of allowing infants to receive deep and adequate sleep thereby eliminating or drastically reducing breathing pauses and apnea especially in pre-term babies and a device capable of increasing infants' oxygen level and decreasing the number of slow heart rate spells associated with full and pre-term infants.

Yet still, another object of this invention is to disclose an Infant Nurturing System Device capable of reducing hospitalization of premature/sick newborns in neonatal intensive care units, thereby reducing overall hospital and patient expense.

Still further, another object of this invention is to disclose an Infant Nurturing System Device capable of being used in both a hospital and/or a home environment.

In order to provide an understanding of the principles associated with the present invention, reference will now be made to the embodiments illustrated in the drawings and specific language will be use to describe the same. However, no limitation of the scope of the invention is hereby intended. Thus, any alteration and modifications of the inventive features illustrated herein and any additional application of the principle of the present invention as illustrated herein which would normally occur to one skill in the relevant art and having possession of this disclosure are to be considered within the scope of the present invention described herein.

DETAILED DESCRIPTION OF THE INVENTION

Figure 1:
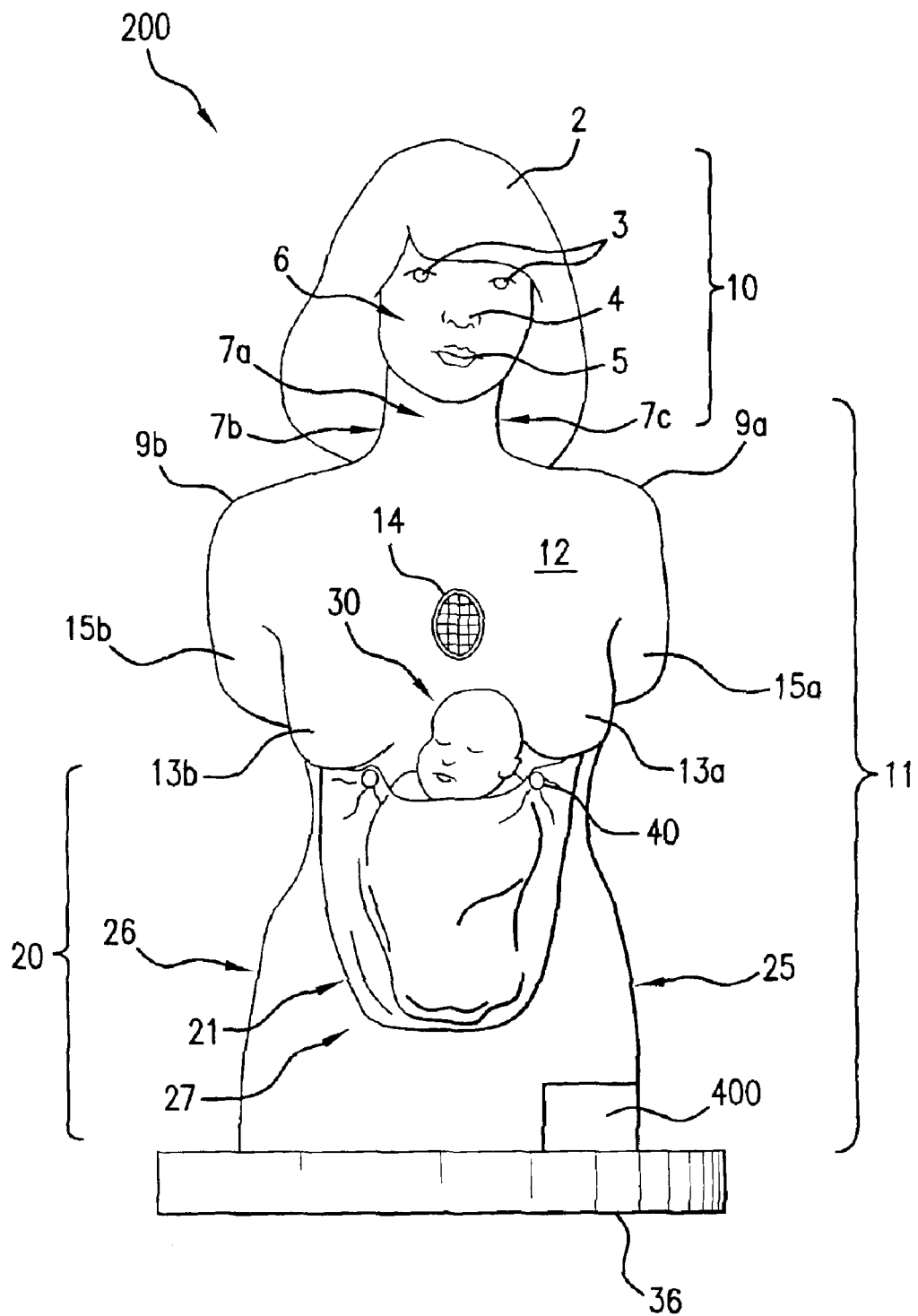
FIG. 1 is a perspective view of a preferred embodiment of the Infant Nurturing Device of the present invention.
Figure 2:
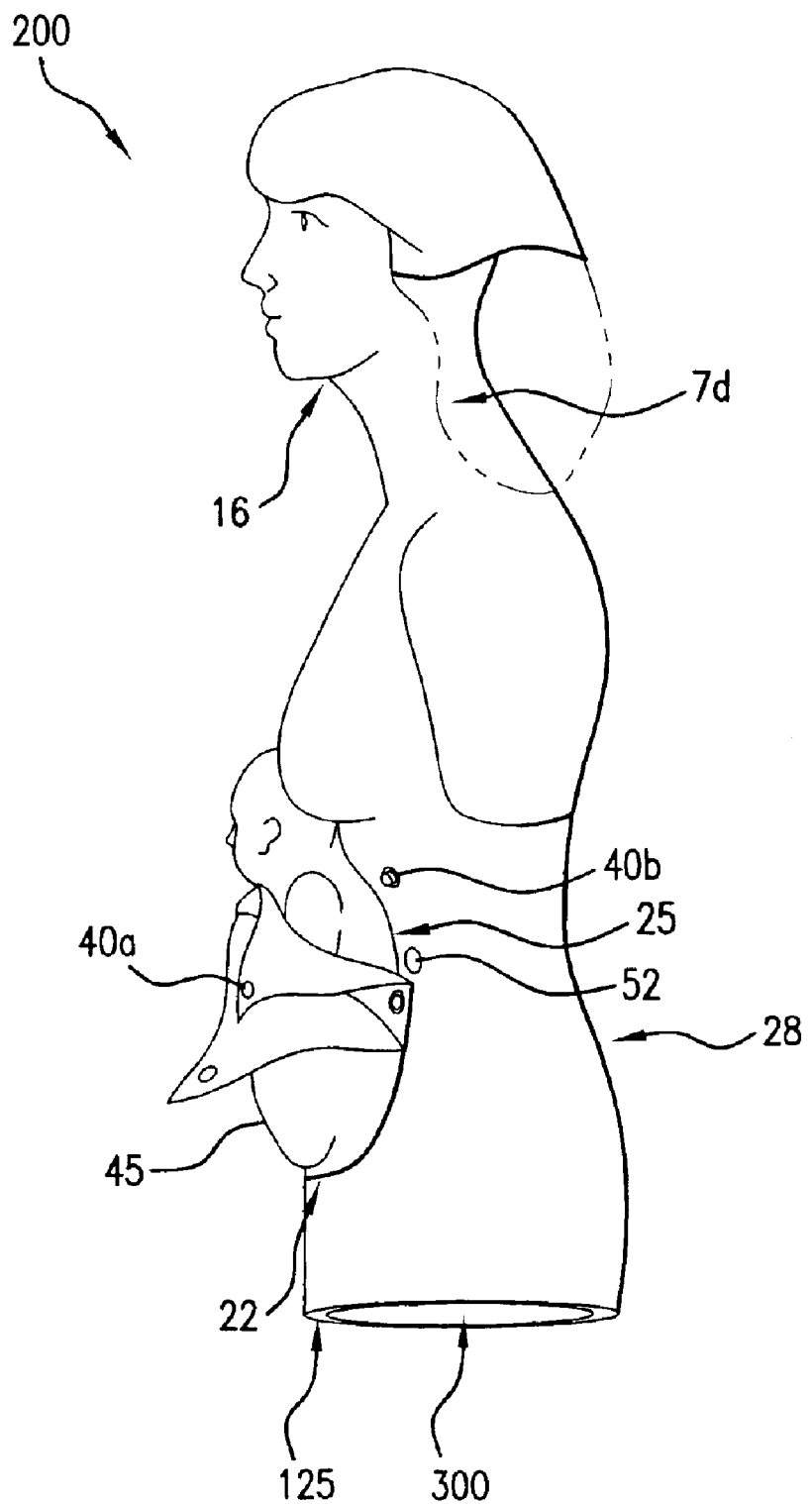
FIG. 2 is a side view, in partial cross section, showing the pouch area and the pouch covering of the Infant Nurturing Device of the present invention.

FIGS. 1 and 2 illustrate an Infant Nurturing Device (200) of the present invention used for promoting emotional and psychological development in newborn infants through parent-infant attachment by transferring simulated parental body temperature, simulated parental heart-beat, simulated parental voice and simulated parental breathing in the absence of biological parents. Referring to FIG. 1, the device (200) is a human-like manikin with a head section (10) having human-like hair (2), a pair of human-like eyes (3), human-like nose (4) and human-like mouth (5). The eyes, nose, and mouth are indentations formed on the face portion (6) of the manikin device (200). The head (10) is connected to a neck (7), proportional to that of a human, having exterior walls (7a), (7b), (7c) and (7d). The neck (7) is connected to the bead (10) at junction (16), wherein each exterior wall of the neck is oppositely connected to the corresponding exterior wall of the lower portion of the head (10). The neck (7) is connected to the shoulder portions (9a) and (9b) and the shoulder portion extend respectively to form the flexible arm members (15a) and (15b), which may be fixed or preferably flexible. During construction, the internal cavity spacing of the head (10) and the neck (7) can remain hollow or preferable filled with appropriate material to maintain rigidity and structure integrity. The device of the present invention may be manufactured from materials such as metal, steel, metal alloy, plastic, reinforced plastic, ceramic, glass, hybrid metal, hybrid plastic-metal, hybrid glass-metal hybrid plastic-glass and other similar materials, etc.

Referring to FIG. 1, the torso portion (11) of the manikin device (200) is generally comprised of a chest portion (12), an abdomen portion (20), two human-like breast (13a) and (13b) and at least one speaker (14) for transmission of sound from within the internal cavity (300) of the manikin device (200). The abdomen portion (20) of the torso (11) has a built-in "Kangaroo-like" pouch or groove (25) whose surface area is proportion to the external covering of the pouch (21) and which may be curved or flatly designed. The external pouch covering, like the device of the present invention, may be manufactured from materials such as cloth, fabric, textile metal, steel metal, metal alloy, plastic, reinforced plastic, ceramic glass, hybrid metal, hybrid plastic-metal, hybrid glass-metal, hybrid plastic-glass, and other similar materials, etc. An infant (30) is firmly secured within the pouch by a fastening means (40), which includes a male portion (40*b*) attached to the abdomen portion (20) and a corresponding female receptor-portion (40*a*) attached to the external cover of the pouch (21). The fastening means (40) may include receptors with corresponding devices such as clips, buttons, zippers, hinges, secured pins, screws and adhesive fabric, etc.

Referring to FIG. 2, the lining of the external pouch covering (21), which proportionally extends around the surface area of the pouch (25) is attached to the abdomen portion (20) at a detachable intersection (22) and permits detachment of the pouch covering from the pouch area and the abdomen portion of the device (200). Detachment capabilities allow for the pouch covering to be partially or completely removed, for example, when sanitizing the device or during the placement of an infant in the pouch. When an infant (30) is placed within the pouch, the pair of flexible arm members (15*a*) and (15*b*) are capable of being adjusted in such a way to place said members on the external pouch covering to simulate a parent cuddling an infant. In the pouch, an infant is positioned faced-up between the breasts 13*a* and 13*b* and is fastened using fastening means 40 so as to keep the infant comfortable and in an upright position.

Still referring to FIGS. 1 and 2, which is the first embodiment of the present invention, the manikin device (200) with base support (36) is designed to sit upright such that an infant (30) positioned within the pouch of the manikin device is made to believe that it is being carried by a parent. The base support may include a bed, a table, a desk and a couch, etc., or lower extremities capable of holding the device in an upright position. During operation, the manikin device is placed in an upright position and an external control panel (400) manufactured directly on an external portion of the device (200) is used for operating and controlling built-in components located within the internal cavity (300) of the device.

Figure 4:
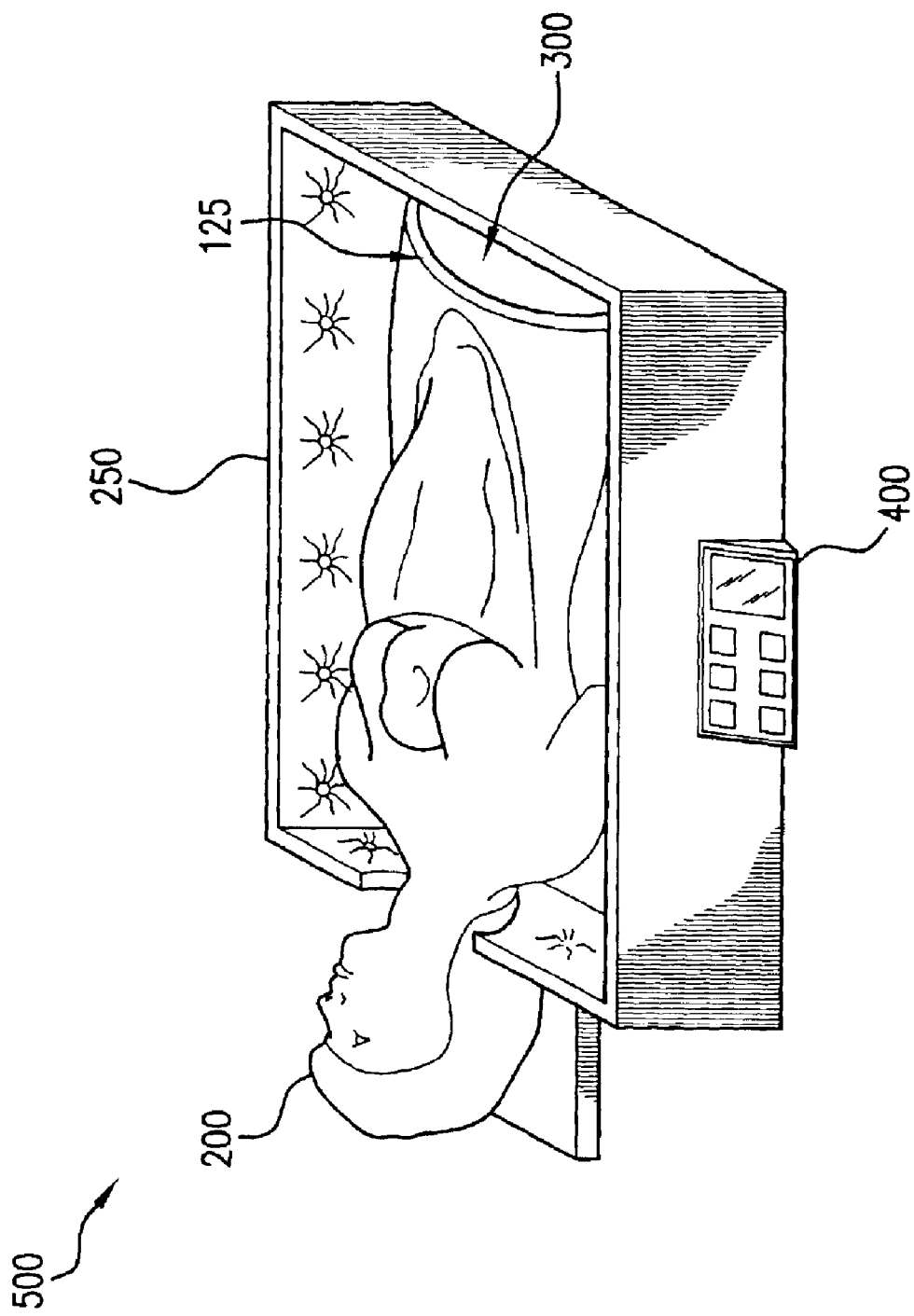
FIG. 4 is a perspective view of another preferred embodiment of the Infant Nurturing Device of the present invention.

Referring to FIG. 4, which is the second embodiment of the present invention, the Infant Nurturing Device (500) comprises the identical manikin device (200) of FIGS. 1 and 2 and a crib (250) for placing the manikin device in a resting, horizontal position. Similar to the first embodiment, when in operation, an infant (30) facing upwards is placed in the pouch area (25) under the external pouch covering (21) of the device (500) between breasts (13*a*) and (13*b*) and is fastened using the fastening means 40. Unlike the first embodiment wherein the device (200) is in an upright position and control panel (400) is directly attached thereon, the device of this embodiment is in a horizontal, resting position within the crib (250), and the control panel (400) for controlling the built-in components within the internal cavity (300) is positioned on the crib rather than directly on the manikin device.

Referring to FIGS. 1, 2 & 4, the abdomen portion (20) encasing the internal cavity (300) includes a front-end casing wall-member (27) corresponding in shape and oppositely positioned to a rear-end casing wall-member (28), and a right-side casing wall-member (26) corresponding in shape and oppositely positioned to a left-side casing wall-member (25). The casing wall-members are manufactured to form the single external abdomen casing portion (20) of the present invention simulating a circular, human-like abdomen. The internal cavity (300) is separated from the external abdomen casing by a peripheral diaphragm-member (125), so positioned for protecting the external abdomen casing (20) from the internal mechanical and electrical stresses associated with operating the built-in components within the internal cavity.

Figure 3:
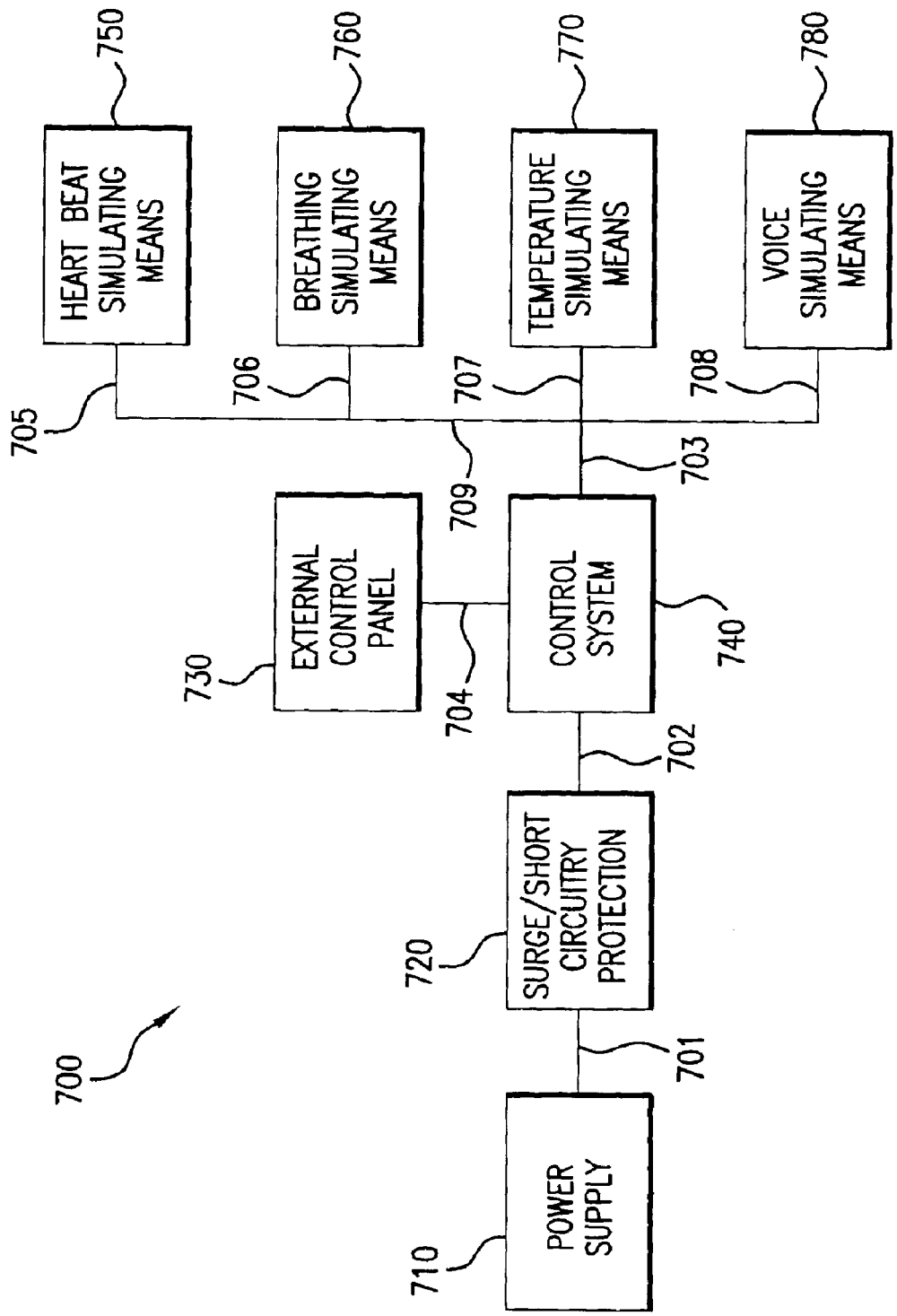
FIG. 3 is a schematic illustration of built-in connected components within the internal cavity of the Infant Nurturing Device of the present invention.

Referring to FIG. 3, the internal cavity of the manikin (300) includes a plurality of connected built-in components (700) for providing emotional and psychological development in newborn infants. The built-in components are composed of a means for simulating parental heart-beat (750), a means for simulating parental breathing (760), a means for simulating parental temperature (770) and a means for simulating parental voice (780). The means for simulating heartbeat, breathing, temperature and voice are electrically coupled in series to a single, central, electrical-connecting member (709) by individualized electrical connecting members (705), (706), (707) and (708) respectively.

The central electrical connecting member (709) through connecting member (703) is electrically coupled to a controller (740), which in turn has one end electrically coupled to an external control panel (730) through connecting member (704). Alternatively, each simulating means can be coupled individually to separate controllers and/or external control panels. Thus, the invention anticipates built-in means comprising individualized connecting members (705), (706), (707) and (708) electrically coupled directly to individualized controllers (740), which are then electrically coupled to individualized external control panels (730).

The other end of the controller is electrically coupled through connecting member (702) to a surge protector (720), which receives power from a power supply (710) through connecting member (701). The controller is capable of activating and/or deactivating any combination of built-in component means continuously or intermittently during operation of the device. The plurality of built-in means is powered by a single power supply (710), which may be a rechargeable battery source or power source supplied directly from electrical outlets. The power supply is connected to a surge circuitry protector (720) to protect against power fluctuations and short circuitry.

Pursuant to FIG. 3, the voice generating means (780) may comprise of a simple built-in cassette or digital disk player, preferably in the manikin's head, although other position on the device would suffice, having at least an external speaker (14) as illustrated in FIG. 1, for sounding the prerecorded, soothing voice and/or conversations of a parent such as a mother. The prerecorded voice and/or conversation could be that of siblings or other family members. The cassette player or digital disk player voice generating means can also be used to play music in the absence of parents or family members' voice and/or conversation. Additionally, the voice generating means (780) may comprise of a prerecorded chip having a generic voice and/or conversation simulating that of a parent or other family relatives.

The temperature generating means (770) for simulating a parent's body temperature for emotional and psychological development of a full or pre-term infant may include at least one of two forms of heat generating technologies. First the device (770) could be fitted with conventional incubator technology which circulates heated, humidified air or incubators for intensive care use, intended for problematic cases of ill and pre-term infants, which are generally provided with infrared-radiation heating means. Second, the device could be fitted with a heating pad or embedded heating coils within the pouch surface area (25) for regulating an infant's body temperature when in use. If an incubator temperature generating means is employed, heated air controlled by controller (740) is convectively transported from the inner cavity (300) through outlets (52) preferably within the pouch area as illustrated in FIG. 2. If, however, the heating pad/embedded coil approach is used the pouch surface area temperature would be heated-up and controlled by controller (740) to simulate a parent's body temperature. Other forms of heating technologies well known in the art may be used in the device of the present invention to simulate a parent's normal body temperature and/or provide adequate temperature for early infant development.

Still referring to FIG. 3, the heartbeat generating means (750) for simulating a parent's heartbeat for promoting emotional and psychological development in full or pre-term infants may comprise of a simple built-in cassette or digital disk player with external speaker (14) for playing the prerecorded heartbeat of an individual, preferably the infant's mother. Other well-known heartbeat simulating devices may be used, such as battery powered transistorized oscillator circuit device with built-in speaker (14) capable of producing output pulses at a predetermined rate of cycles per minute to produce sounds simulating a heartbeat, and a vibrator casing device with enclosed electromagnetic device forming a pulsation assembly which vibrates against the diaphragm (125) to simulate a parent's heartbeat.

The breathing generating means (760) for simulating a parent's breathing may comprise of an inflating means such as a pump and a deflating means such as a control-pneumatic valve, which periodically supplies the entire internal cavity or a section thereof with air and periodically removes the inflated air respectively. The breathing generating means of the present invention may also comprise of a mechanical or electromagnetic device, such as a motor, coupled to the entire interior diaphragm (125) or a section thereof of the internal cavity (300) by the use of a cord, wherein when the motor is intermittently energized at periodic intervals to pull the diaphragm inwards, and the motor is then disabled to allow the resilience to unwind the cord so that the diaphragm returns to its unwind equilibrium position, but at a slower rate than its inward stroke to simulate a true heart beat. Other applicable means of simulating breathing may be used in the device of the present invention to simulate a parent's breathing rhythm.

During operation, the Infant Nurturing Device's torso portion (11) of the present invention may be fitted with a parent's worn clothing bearing the scent of the parent. The placement of worn clothing bearing scent would assist with emotional and psychological development of an infant during the performance of "Kangaroo Care" attachment, as contemporary research has established that an infant partially recognizes his or her biological parents through their respective scent or odor.

The present invention anticipates all future equivalent improvements such as a device capable of placing an infant face-down in the pouch, motorized upright device capable of forward, lateral and reverse movements to simulate the movement of a parent while performing "Kangaroo Care" attachment, and a device comprising a crib wherein the built-in components are located within the crib instead of the internal cavity of the manikin device, etc. While an illustrative embodiment of the invention has been described, it is, of course understood that various modifications of the invention will be obvious to those of ordinary skill in the art. Such modifications are within the spirit and scope of the invention, which are limited and defined only by the appended claims.

What is claimed is:

1. An infant nurturing device, "Edith, A mother in Absentia", capable of performing parent-infant "Kangaroo Care" attachment in the absence of biological parents comprising:
   (a) a head portion;
   (b) a neck portion;
   (c) a torso portion;
   (d) a base support portion;
   (e) a pouch area;
   (f) an internal cavity separated from external outer abdomen casing portions by a separation diaphragm member; and
   (g) an electrical control panel for controlling voice, temperature, breathing and heartbeat simulations.

2. The infant nurturing device according to claim 1, wherein said device further comprises a corresponding external pouch covering for enclosing full-term and pre-term infants when in use.

3. The infant nurturing device according to claim 1, wherein said torso portion further comprises a chest portion and an abdomen portion.

4. The infant nurturing device according to claim 3, wherein said head portion further comprises human-like hair, a pair of human-like eyes, human-like nose, human-like mouth, and wherein said base support further comprises a pair of lower extremities.

5. The infant nurturing device according to claim 4, wherein said internal cavity further comprises:
   (a) a voice simulating means
   (b) a temperature simulating means
   (c) a breathing simulating means; and
   (d) a heart beat simulating means.

6. The infant nurturing device according to claim 5 wherein said voice, temperature, breathing and heartbeat simulating means are electrically coupled to a central control system, a first end of said control system is electrically coupled to an external control panel directly attached on said device, and a second end of said control system is electrically coupled to a surge circuitry protector, wherein said protector is electrically coupled to a power supply.

7. The infant nurturing device according to claim 6, wherein said device further comprises the following:
   (a) said power supply consisting of electrical outlets and rechargeable batteries;
   (b) said device manufactured from materials consisting of metal, steel, metal alloy, plastic, reinforced plastic, ceramic, glass, hybrid metals, hybrid plastic-metal, hybrid glass-metal and hybrid plastic-glass;
   (c) said external pouch covering is manufactured from materials consisting of cloth, fabric, textile, metal, steel, metal alloy, plastic, reinforced plastic, ceramic, glass, hybrid metals, hybrid plastic-metal, hybrid glass-metal and hybrid plastic-glass;
   (d) said heartbeat simulating means consisting of cassette player with prerecorded heartbeat, disk player with prerecorded heartbeat, battery powered transistorized oscillators and vibrator casing;
   (e) said temperature simulating means consisting of heated-humidified air incubator based technology, infrared incubator based technology, heating pad based technology and embedded heating coil based technology;
   (f) Said voice simulating means consisting of cassette player with prerecorded voice, digital disk player with prerecorded voice, and prerecorded chip; and
   (g) Said breathing simulating means consisting of a pump-pneumatic valve system and an electromagnetic, motorized cord device.

8. The infant nurturing device according to claim 7, wherein said device is fitted with flexible arm members.

9. The infant nurturing device according to claim 8, wherein said device is motorized and fitted with worn parental clothing during use.

10. An infant nurturing device, "Edith, A mother in Absentia", capable of performing parent-infant "Kangaroo Care" attachment in the absence of biological parents comprising:
   (a) a head portion;
   (b) a neck portion;
   (c) a torso portion;
   (d) a base support portion;
   (e) a pouch area; and
   (f) an electrical control panel for controlling voice, temperature, breathing and heartbeat simulations; and
   (g) a crib having four walls for placing said infant nurturing device comprising a head portion, a neck portion, a torso portion, and a pouch area in a horizontal resting position.

11. The infant nurturing device according to claim 10, wherein said device further comprises a pouch area, and a corresponding external pouch covering for enclosing full-term and pre-term infants when in use.

12. The infant nurturing device according to claim 11, wherein said torso portion further comprises a chest portion and an abdomen portion.

13. The infant nurturing device according to claim 12, wherein said head portion further comprises human-like hair, a pair of human-like eyes, human-like nose, human-like mouth, and wherein said base support further comprises a pair of lower extremities.

14. The infant nurturing device according to claim 13, wherein the abdomen portion further comprises an internal cavity separated from external outer abdomen casing portions by a separation diaphragm member.

15. The infant nurturing device according to claim 14, wherein said internal cavity further comprises:
   (a) a voice simulating means
   (b) a temperature simulating means
   (c) a breathing simulating means; and
   (d) a heart beat simulating means.

16. The infant nurturing device according to claim 15, wherein said voice, temperature, breathing and heartbeat simulating means are electrically coupled to a central control system, a first end of said control system is electrically coupled to an external control panel directly attached on said crib, and a second end of said control system is electrically coupled to a surge circuitry protector, wherein said protector is electrically coupled to a power supply.

17. The infant nurturing device according to claim 16, wherein said device further comprises the following:
   (a) said power supply consisting of electrical outlets and rechargeable batteries;
   (b) said device manufactured from materials consisting of metal, steel, metal alloy, plastic, reinforced plastic, ceramic, glass, hybrid metals, hybrid plastic-metal, hybrid glass-metal and hybrid plastic-glass;
   (c) said external pouch covering is manufactured from materials consisting of cloth, fabric, textile, metal, steel, metal alloy, plastic, reinforced plastic, ceramic, glass, hybrid metals, hybrid plastic-metal, hybrid glass-metal and hybrid plastic-glass;
   (d) said heartbeat simulating means consisting of cassette player with prerecorded heartbeat, disk player with prerecorded heartbeat, battery powered transistorized oscillators and vibrator casing;
   (e) said temperature simulating means consisting of heated-humidified air incubator based technology, infrared incubator based technology, heating pad based technology and embedded heating coil based technology;
   (f) said voice simulating means consisting of cassette player with prerecorded voice, digital disk player with prerecorded voice, and prerecorded chip; and
   (g) said breathing simulating means consisting of a pump-pneumatic valve system and an electromagnetic, motorized cord device.

18. The infant nurturing device according to claim 17, wherein said device is fitted with flexible arm members.

19. The infant nurturing device according to claim 18, wherein said device is fitted with worn parental clothing during use.

* * * * *